US011937940B2

(12) United States Patent
Thaveeprungsriporn et al.

(10) Patent No.: US 11,937,940 B2
(45) Date of Patent: Mar. 26, 2024

(54) DEVICES AND METHODS FOR STRESS ASSESSMENT USING PHYSIOLOGICAL DATA

(71) Applicant: Nitto Denko Corporation, Osaka (JP)

(72) Inventors: Visit Thaveeprungsriporn, Singapore (SG); Shoko Trepetch, Bangkok (TH); Amornsri Khitwongwattana, Bangkok (TH); Anyamanee Pornpanvattana, Bangkok (TH); Ananya Chaithanaboon, Bangkok (TH)

(73) Assignee: Nitto Denko Corporation (JP)

( * ) Notice: Subject to any disclaimer, the term of this patent is extended or adjusted under 35 U.S.C. 154(b) by 842 days.

(21) Appl. No.: 16/976,933

(22) PCT Filed: Feb. 28, 2019

(86) PCT No.: PCT/SG2019/050110
§ 371 (c)(1),
(2) Date: Aug. 31, 2020

(87) PCT Pub. No.: WO2019/168473
PCT Pub. Date: Sep. 6, 2019

(65) Prior Publication Data
US 2021/0007667 A1    Jan. 14, 2021

(30) Foreign Application Priority Data
Mar. 2, 2018    (SG) .............................. 10201801851S

(51) Int. Cl.
*A61B 5/00*    (2006.01)
*A61B 5/024*    (2006.01)

(52) U.S. Cl.
CPC .......... *A61B 5/4884* (2013.01); *A61B 5/0006* (2013.01); *A61B 5/0022* (2013.01);
(Continued)

(58) Field of Classification Search
CPC .......... A61B 2560/0209; A61B 5/0022; A61B 5/02405; A61B 5/1118; A61B 5/165;
(Continued)

(56) References Cited

U.S. PATENT DOCUMENTS

2012/0232414 A1    9/2012    Mollicone et al.
2017/0071551 A1    3/2017    Jain et al.

FOREIGN PATENT DOCUMENTS

CN    107661094 A    2/2018
EP    2911579 A1    9/2015
(Continued)

OTHER PUBLICATIONS

Extended European Search Report including Written Opinion for Application No. 19760611.4 dated Nov. 9, 2021, pp. 1-11.
(Continued)

*Primary Examiner* — Jon Eric C Morales
(74) *Attorney, Agent, or Firm* — Lerner David LLP

(57) ABSTRACT

The present disclosure generally relates to a measurement device (110) and a method (200/300) for stress assessment of a user. The measurement device (110) comprises: a sensor module for measuring a number of sets of physiological data, each set of measured during a time period; a database (112) for storing the data; a display module (116) for displaying visual information (400/420/440). The method (200/300) comprises determining a stress parameter for each set of data for comparison against a predefined stress reference; identifying a first stress parameter for a current time period; generating a stress alert in response to a determination that predefined stress conditions are satisfied based on at least the first stress parameter; and displaying the visual information (400/420/440) corresponding to the stress alert and assistive to relieving the stress state, wherein the stress conditions are satisfied if the first stress parameter is indica-
(Continued)

tive of a stress state of the user relative to the predefined stress reference.

20 Claims, 8 Drawing Sheets

(52) U.S. Cl.
CPC .......... *A61B 5/02416* (2013.01); *A61B 5/742* (2013.01); *A61B 5/746* (2013.01)

(58) Field of Classification Search
CPC ..... A61B 5/4884; A61B 5/681; A61B 5/7203; A61B 5/746; A61B 2503/10; A61B 5/0006; A61B 5/0013; A61B 5/024; A61B 5/02416; A61B 5/02438; A61B 5/0533; A61B 5/349; A61B 5/352; A61B 5/4812; A61B 5/486; A61B 5/6833; A61B 5/6898; A61B 5/7207; A61B 5/7225; A61B 5/7235; A61B 5/7257; A61B 5/7275; A61B 5/7278; A61B 5/7282; A61B 5/7405; A61B 5/742; A61B 5/743; A61B 5/7455; A61B 5/7475; G16H 40/67; G16H 40/60; G16H 40/63
See application file for complete search history.

(56) References Cited

FOREIGN PATENT DOCUMENTS

| JP | 201053307 A | 3/2010 |
|---|---|---|
| KR | 20160028329 A | 3/2016 |
| WO | 2008122928 A1 | 10/2008 |
| WO | 2017217600 A1 | 12/2017 |

OTHER PUBLICATIONS

International Search Report for Application No. PCT/SG2019/050110 dated May 24, 2019, 3 pages.

Jha, et al., "Wearable anger-monitoring system," ICT Express, Jul. 28, 2017, pp. 194-198, vol. 4.

Lyu, et al., "Measuring Photoplethysmogram-Based Stress-Induced Vascular Response Index to Assess Cognitive Load and Stress," The 33rd Annual ACM Conference on Human Factors in Computing Systems, Apr. 18-23, 2015, pp. 1-10.

Wu, et al., "Combination of Wearable Multi-Biosensor Platform and Resonance Frequency Training for Stress Management of the Unemployed Population," Sensors, Sep. 27, 2012, pp. 13225-13248, vol. 12, No. 10.

DEVICES AND METHODS FOR STRESS ASSESSMENT USING PHYSIOLOGICAL DATA

CROSS REFERENCE TO RELATED APPLICATION(S)

The present application is a national phase entry under 35 U.S.C. § 371 of International Application No. PCT/SG2019/050110 filed Feb. 28, 2019, which claims the benefit of Singapore Patent Application No. 10201801851S filed on Mar. 2 2018, the disclosures of which are incorporated by reference herein.

TECHNICAL FIELD

The present disclosure generally relates to devices and methods for stress assessment. More particularly, the present disclosure describes various embodiments of devices and methods for stress assessment of a user or person using physiological data measured from the user.

BACKGROUND

Various types of measurement or sensing devices have emerged to help people to self-monitor their health condition by measuring physiological data from their bodies. The physiological data includes blood pressure, heart rate, and heart rate variability. However, these devices may not provide sufficiently accurate self-monitoring of health conditions, such as for stress assessment. Furthermore, many measurement or sensing devices do not provide useful feedback to people on managing their stress.

Therefore, in order to address or alleviate at least one of the aforementioned problems and/or disadvantages, there is a need to provide improved devices and methods for stress assessment.

SUMMARY

According to a first aspect of the present disclosure, there is a measurement device for stress assessment of a user. The measurement device comprises: a sensor module comprising a photoplethysmography (PPG) sensor for measuring, from the user, a number of sets of physiological data, each set of physiological data measured during a discrete time period; a database for storing the physiological data; a display module comprising a set of graphical user interface (GUI) portions for displaying visual information from the stress assessment based on the physiological data; and a processor. The processor is configured for: determining a stress parameter for each set of physiological data for comparison against a predefined stress reference; identifying a first stress parameter for a current time period; generating a stress alert in response to a determination that predefined stress conditions are satisfied based on at least the first stress parameter; and communicating the stress alert to the display module for displaying, on at least one of the GUI portions, the visual information corresponding to the stress alert and assistive to the user in relieving the stress state, wherein the stress conditions are satisfied if the first stress parameter is indicative of a stress state of the user relative to the predefined stress reference.

According to a second aspect of the present disclosure, there is a computerized method performed by a measurement device for stress assessment of a user, as well as non-transitory computer-readable storage medium having stored thereon instructions that, when executed, cause a processor of the measurement device to perform the method. The method comprises: retrieving, from a database of the measurement device, a number of sets of physiological data measured from the user, each set of physiological data measured during a discrete time period; determining a stress parameter for each set of physiological data for comparison against a predefined stress reference; identifying a first stress parameter for a current time period; generating a stress alert in response to a determination that predefined stress conditions are satisfied based on at least the first stress parameter; and displaying, on at least one graphical user interface (GUI) portion, visual information corresponding to the stress alert and assistive to the user in relieving the stress state, wherein the stress conditions are satisfied if the first stress parameter is indicative of a stress state of the user relative to the predefined stress reference.

According to a third aspect of the present disclosure, there is a computerized method performed by an electronic device for stress assessment of a user, as well as non-transitory computer-readable storage medium having stored thereon instructions that, when executed, cause a processor of the electronic device to perform the method. The method comprises: receiving, from a measurement device, a measurement dataset comprising a number of sets of physiological data measured from the user, each set of physiological data measured during a discrete time period; storing the measurement dataset on a database of the electronic device; determining a stress parameter for each set of physiological data for comparison against a predefined stress reference; identifying a first stress parameter for a current time period; generating a stress alert in response to a determination that predefined stress conditions are satisfied based on at least the first stress parameter; and displaying, on at least one graphical user interface (GUI) portion, visual information corresponding to the stress alert and assistive to the user in relieving the stress state, wherein the stress conditions are satisfied if the first stress parameter is indicative of a stress state of the user relative to the predefined stress reference.

Devices and methods for stress assessment according to the present disclosure are thus disclosed herein. Various features, aspects, and advantages of the present disclosure will become more apparent from the following detailed description of the embodiments of the present disclosure, by way of non-limiting examples only, along with the accompanying drawings.

DETAILED DESCRIPTION

Figure 1A:
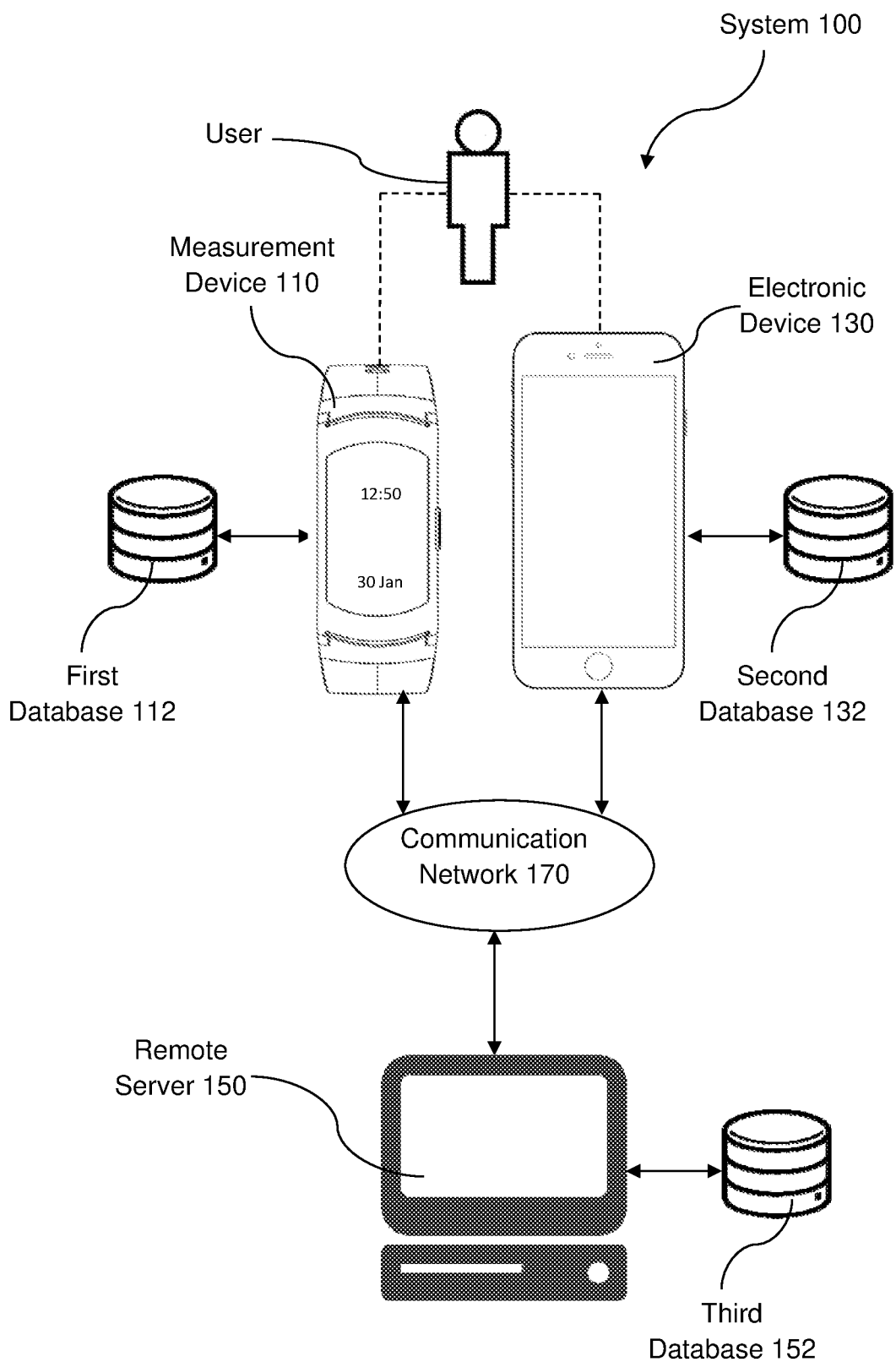
FIG. 1A is a schematic illustration of a system comprising a measurement device, an electronic device, and a remote server for stress assessment of a user, in accordance with embodiments of the present disclosure.

For purposes of brevity and clarity, descriptions of embodiments of the present disclosure are directed to a system and method for securing data communication between computers, in accordance with the drawings. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognized by an individual having ordinary skill in the art, i.e. a skilled person, that the present disclosure may be practiced without specific details, and/or with multiple details arising from combinations of aspects of particular embodiments. In a number of instances, well-known systems, methods, procedures, and components have not been described in detail so as to not unnecessarily obscure aspects of the embodiments of the present disclosure.

In embodiments of the present disclosure, depiction of a given element or consideration or use of a particular element number in a particular figure or a reference thereto in corresponding descriptive material can encompass the same, an equivalent, or an analogous element or element number identified in another figure or descriptive material associated therewith.

References to "an embodiment/example", "another embodiment/example", "some embodiments/examples", "some other embodiments/examples", and so on, indicate that the embodiment(s)/example(s) so described may include a particular feature, structure, characteristic, property, element, or limitation, but that not every embodiment/example necessarily includes that particular feature, structure, characteristic, property, element or limitation. Furthermore, repeated use of the phrase "in an embodiment/example" or "in another embodiment/example" does not necessarily refer to the same embodiment/example.

The terms "comprising", "including", "having", and the like do not exclude the presence of other features/elements/steps than those listed in an embodiment. Recitation of certain features/elements/steps in mutually different embodiments does not indicate that a combination of these features/elements/steps cannot be used in an embodiment.

As used herein, the terms "a" and "an" are defined as one or more than one. The use of "/" in a figure or associated text is understood to mean "and/or" unless otherwise indicated. The term "set" is defined as a non-empty finite organization of elements that mathematically exhibits a cardinality of at least one (e.g. a set as defined herein can correspond to a unit, singlet, or single-element set, or a multiple-element set), in accordance with known mathematical definitions. The recitation of a particular numerical value or value range herein is understood to include or be a recitation of an approximate numerical value or value range.

As used herein, the terms "component", "module," "system", "interface", and the like are generally intended to refer to a computer-related entity, either hardware, a combination of hardware and software, software, or software in execution. For example, a component or a module may be, but is not limited to being, a process running on a processor, a processor, an object, an executable, a thread of execution, a program, and/or a computer. By way of illustration, both an application running on a controller and the controller can be a component/module. One or more components/modules may reside within a process and/or thread of execution. A component/module may be localized on one computer and/or distributed among a plurality of computers.

In representative or exemplary embodiments of the present disclosure, there is a system 100 comprising a measurement or sensing device 110, an electronic device 130, and a remote server 150 communicatively connected via a communication network 170, as illustrated in FIG. 1A. The measurement device 110 is configured for measuring physiological data from a user and for stress assessment of the user based on the physiological data. The electronic device 130 is configured for stress assessment of the user based on physiological data received from the measurement device 110 via the communication network 170. The remote server 150 is configured for stress assessment of the user, particularly for assessment of a long-term or chronic stress state, based on physiological data received from the measurement device 110 and/or the electronic device 130 together with historical physiological data of the user.

The measurement device 110 comprises a first database 112 residing locally thereon. The electronic device 130 comprises a second database 132 residing locally thereon. The remote server 150 comprises a third database 152 residing locally thereon. The databases 112, 132, and 152 may have data storage devices, flash storage memories, hard drives, etc. for storing the physiological data.

The measurement device 110 is a physiological monitoring device connected or connectable to a user for measuring and collecting physiological data of the user. The physiological data is subsequently used for stress assessment of the user. The physiological data is related or derived from vascular activity of the user, such as volumetric changes resulting from fluctuations in blood flow in the blood vessels in the region where the measurement device 110 is attached. The measurement device 110 may be in the form of a wearable device that is worn or attached to the user, such as at the fingertip, wrist, any portion of the arm, or any portion of the neck. For example, the measurement device 110 is in the form of a watch wearable on the user's wrist. The measurement device 110 may be configured to measure physiological data only if there is sufficient battery power therein.

The physiological data includes data on vital signs of the user measureable from the vascular activity, such as but not limited to, heart rate, heart rate variability, blood pressure, pulse shape variability, and the like and any combination thereof. Pulse shape variability can be referred to as a standard deviation of the vital sign feature derived from a pulse shape of the input physiological signal (e.g. a PPG signal), which may be calculated based on time interval information, skewness, magnitude, integral and differential information, a frequency component, or their derivatives of a pulse for example.

The measurement device 110 comprises a sensor module for measuring the physiological data. Specifically, the sensor module includes a photoplethysmography (PPG) sensor for measuring, from the user, a number of sets (i.e. at least one set) of physiological data, each set of physiological data measured during a discrete time period. For example, the sets of physiological data may be measured in time periods ranging from 1 minute to 5 minutes, although other time periods are possible. In some embodiments, the PPG sensor is a pulse oximeter sensor having an illumination element, e.g. a light emitting diode (LED), and at least two photodetectors/photodiodes for measuring physiological data resulting from vascular activity in the user. The illumination element may be positioned between or adjacent to the two photodetectors.

In each cardiac cycle, the heart pumps blood to the periphery (e.g. wrist and digits) of the body through a pressure pulse. The pressure pulse is sufficient to distend the blood vessels in the subcutaneous tissue in the body skin, thereby changing the blood volume of the subcutaneous tissue in the body skin. The pulse oximeter sensor measures the vascular activity resulting from blood circulation in the body. Specifically, the pulse oximeter sensor measures the amount of oxygen in blood indirectly by determining the oxygen saturation level ($SO_2$) of the haemoglobin in blood and also measures changes in blood volume in the body skin. The change in volume caused by the pressure pulse can be detected by illuminating the skin with the illumination element of the pulse oximeter sensor and then measuring the amount of light either transmitted or reflected to the photodetectors/photodiodes. The measurement device 110 is worn or attached close to the body skin of the user so that the PPG or pulse oximeter sensor can illuminate the skin and detect the changes in light absorption to thereby measure the physiological data. The physiological data is measured as a photoplethysmogram having at least one series of data signals or waveform, i.e. a series of physiological data.

The electronic device 130 is a computer or computing device which is operated by the user. Some non-limiting examples of the electronic device 130 include a desktop device, mobile device, personal digital assistant (PDA), mobile phone, tablet, phablet, laptop computer, and any other electronic communication which may have processors, microprocessors, central processing units, or controllers. The electronic device 130 is communicable with the measurement device 110 and the remote server 150 via the communication network 170, such as for sharing of the physiological data.

The remote server 150 is a computer server that is located remotely away from the electronic device 130, i.e. not sharing the same local network of the electronic device 130. The remote server 150 is a physical or cloud data processing system on which a server program runs. The server may be implemented in hardware or software, or a combination thereof. The server includes computers, laptops, mini-computers, mainframe computers, any non-transient and tangible machines that can execute a machine-readable code, cloud-based servers, distributed server networks, and a network of computer systems.

The communication network 170 is a medium or environment through which content, notifications, and/or messages are communicated among various entities, including the measurement device 110, the electronic device 130, and the remote server 150. Some non-limiting examples of the communication network 170 include a virtual private network (VPN), wireless fidelity (Wi-Fi) network, light fidelity (Li-Fi) network, local area network (LAN), wide area network (WAN), metropolitan area network (MAN), satellite network, Internet, fiber optic network, coaxial cable network, infrared (IR) network, radio frequency (RF) network, and any combination thereof. Connection to the communication network 170 may be in accordance with various wired and wireless communication protocols, such as Transmission Control Protocol/Internet Protocol (TCP/IP), User Datagram Protocol (UDP), 2nd to 5th Generation (2G to 5G), Long Term Evolution (LTE), Long Range (LoRa), and any combination thereof. Each of the measurement device 110, the electronic device 130, and the remote server 150 comprises a data communication or transceiver module to communicate and send/receive data over the communication network 170. Some non-limiting examples of a transceiver module include an antenna module, a radio frequency transceiver module, a wireless transceiver module, a Bluetooth transceiver module, an Ethernet port, a Universal Serial Bus (USB) port, or any combination thereof. Additionally, communications through the communication network 170 may be secured by protocols such as Hypertext Transfer Protocol Secure (HTTPS) and/or implemented with network security systems such as computing firewalls, as will be readily understood by the skilled person.

In some embodiments, the measurement device 110 is communicable with the electronic device 130 via wireless/contactless communication protocols such as Bluetooth, Wi-Fi, and Near Field Communication (NFC) communication protocols. For example, the measurement device 110 and the electronic device 130 may share the same Wi-Fi network and data is communicable therebetween. The measurement device 110 may also be communicable with the electronic device 130 via wired communications such as USB. The electronic device 130 is communicable with the remote server 150 such as via the Internet. The electronic device 130 thus functions as an intermediary device between the measurement device 110 and the remote server 150, such that the measurement device 110 is communicable with the remote server 150 via the electronic device 130. For example, the measurement device 110 measures the physiological data and stores the physiological data on the first database 112. The measurement device 110 may automatically communicate the physiological data the electronic device 130 and thereby to the remote server 150. Alternatively, the measurement device 110 may first communicate the physiological data to the electronic device 130 for storing on the second database 132, and the electronic device 130 subsequently communicates the physiological data to the remote server 150 at a later time for storing on the third database 152. This may happen if the user is being measured by the measurement device 110 and there is zero or limited network connectivity. In some other embodiments, the measurement device 110 is directly communicable with the remote server 150 such as via the Internet for direct sharing of the physiological data.

Figure 1B:
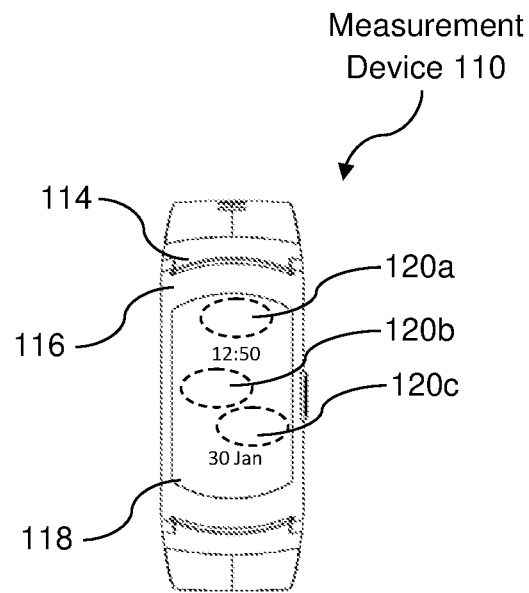
FIG. 1B is a schematic illustration of the measurement device, in accordance with embodiments of the present disclosure.

With reference to FIG. 1B, the measurement device 110 includes a device body 114 and a display module 116. The display module 116 includes a graphical user interface (GUI) 118 having a set of graphical user interface (GUI) portions 120 for displaying visual information from the stress assessment of the user based on the physiological data. The visual information is derived from processing of the physiological data and may be displayed on one or more of the GUI portions 120 or on the entire GUI 118. In some embodiments, the GUI 118 includes a first GUI portion 120a, a second GUI portion 120b, and a third GUI portion 120c. It will be appreciated that each of the GUI portions 120a-c may be rearranged in any location of the GUI 118.

Figure 1C:
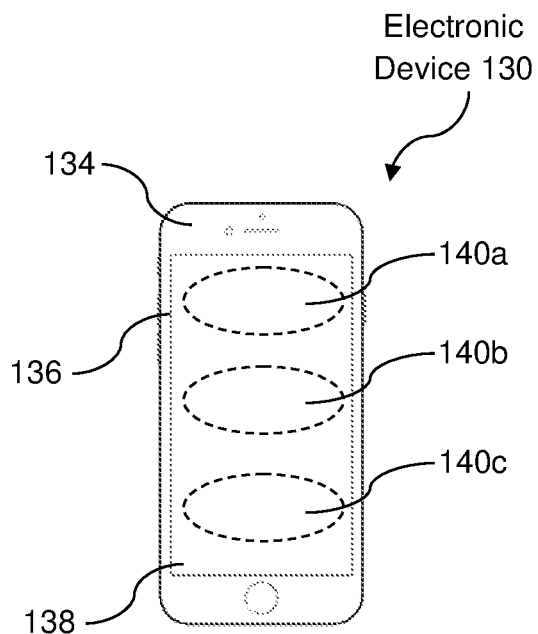
FIG. 1C is a schematic illustration of the electronic device, in accordance with embodiments of the present disclosure.

With reference to FIG. 1C, the electronic device 130 includes a device body 134 and a display module 136. The display module 136 includes a GUI 138 having a set of GUI portions 140 for displaying visual information from the stress assessment of the user based on the physiological data. The visual information is derived from processing of the physiological data and may be displayed on one or more of the GUI portions 140 or on the entire GUI 138. In some embodiments, the GUI 138 includes a first GUI portion 140a, a second GUI portion 140b, and a third GUI portion 140c. It will be appreciated that each of the GUI portions 140a-c may be rearranged in any location of the GUI 138.

In one embodiment, the user downloads a software application, e.g. a mobile app, and installs it on the electronic device 130, e.g. a mobile phone. In another embodiment, the software application is a web or web-based application that is accessible using a browser executed on the electronic device 130. The web or web-based application may be hosted on the remote server 150, such that it can be accessed by multiple users using multiple electronic devices 130. The software application may operate on a subscription basis such that the user is required to pay subscription fees in order to use the stress assessment functions availed by the software application.

The software application is executable on the electronic device 130 for performing stress assessment of the user. The user may need to setup his/her profile if he/she is using the software application for the first time. In this setup or registration procedure, the user inputs a relevant set of personal information including a set of physiological information that may include gender, date of birth, weight, height, job type, and health background. The personal information and physiological information are used to determine reference conditions, e.g. a normal/unstressed state for reference, for stress assessment of the user.

After the registration procedure, the user configures the measurement device 110 to be associated with the electronic device 130, such as by Bluetooth pairing. The association between the measurement device 110 and electronic device 130 enables the measurement device 110 to communicate the measured physiological data to the electronic device 130. The personal information and physiological information together with the reference conditions may also be communicated from the electronic device 130 to the measurement device 110.

Figure 2:
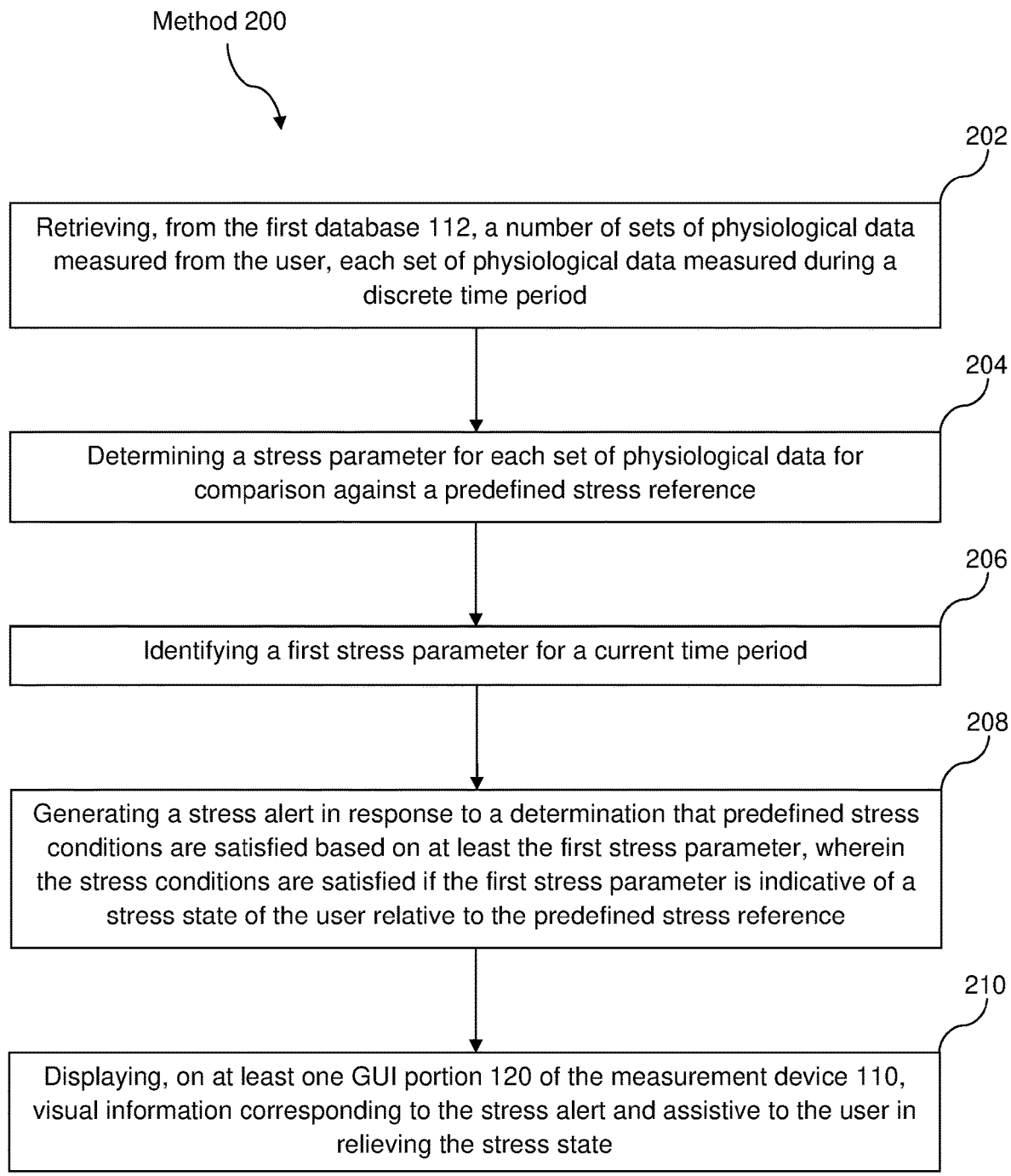
FIG. 2 is a flowchart illustration of a computerized method performed by the measurement device for stress assessment of the user, in accordance with embodiments of the present disclosure.

With reference to FIG. 2, there is shown a computer-implemented or computerized method 200 for stress assessment of the user. The method 200 is implemented on and performed by the measurement device 110 which comprises various modules/components, including a processor for executing program instructions, for performing various steps of the method 200.

The method 200 includes a step 202 of retrieving, from the first database 112, a number of sets (i.e. at least one set) of physiological data measured from the user, each set of physiological data measured during a discrete time period. The method 200 includes a step 204 of determining a stress parameter for each set of physiological data for comparison against a predefined stress reference. The method 200 includes a step 206 of identifying a first stress parameter for a current time period. The method 200 includes step 208 of generating a stress alert in response to a determination that predefined stress conditions are satisfied based on at least the first stress parameter. Specifically, the stress conditions are satisfied if the first stress parameter is indicative of a stress state of the user relative to the predefined stress reference. The method 200 includes a step 210 of displaying, on at least one GUI portion 120 of the measurement device 110, visual information corresponding to the stress alert and assistive to the user in relieving the stress state.

In some embodiments, the measurement device 110 shares the physiological data with the electronic device 130 for the electronic device 130 to perform stress assessment of the user. In one embodiment, the physiological data is measured and stored on the first database 112 before communicating the physiological data to the electronic device 130, such as upon request by the user. In another embodiment, there is an active communication link between the measurement device 110 and the electronic device 130 such that the physiological data is automatically shared with the electronic device 130 immediately or shortly after measurement thereof. Similarly, there may be an active communication link between the electronic device 130 and the remote server 150 such that the physiological data is automatically shared with the remote server 150.

Figure 3:
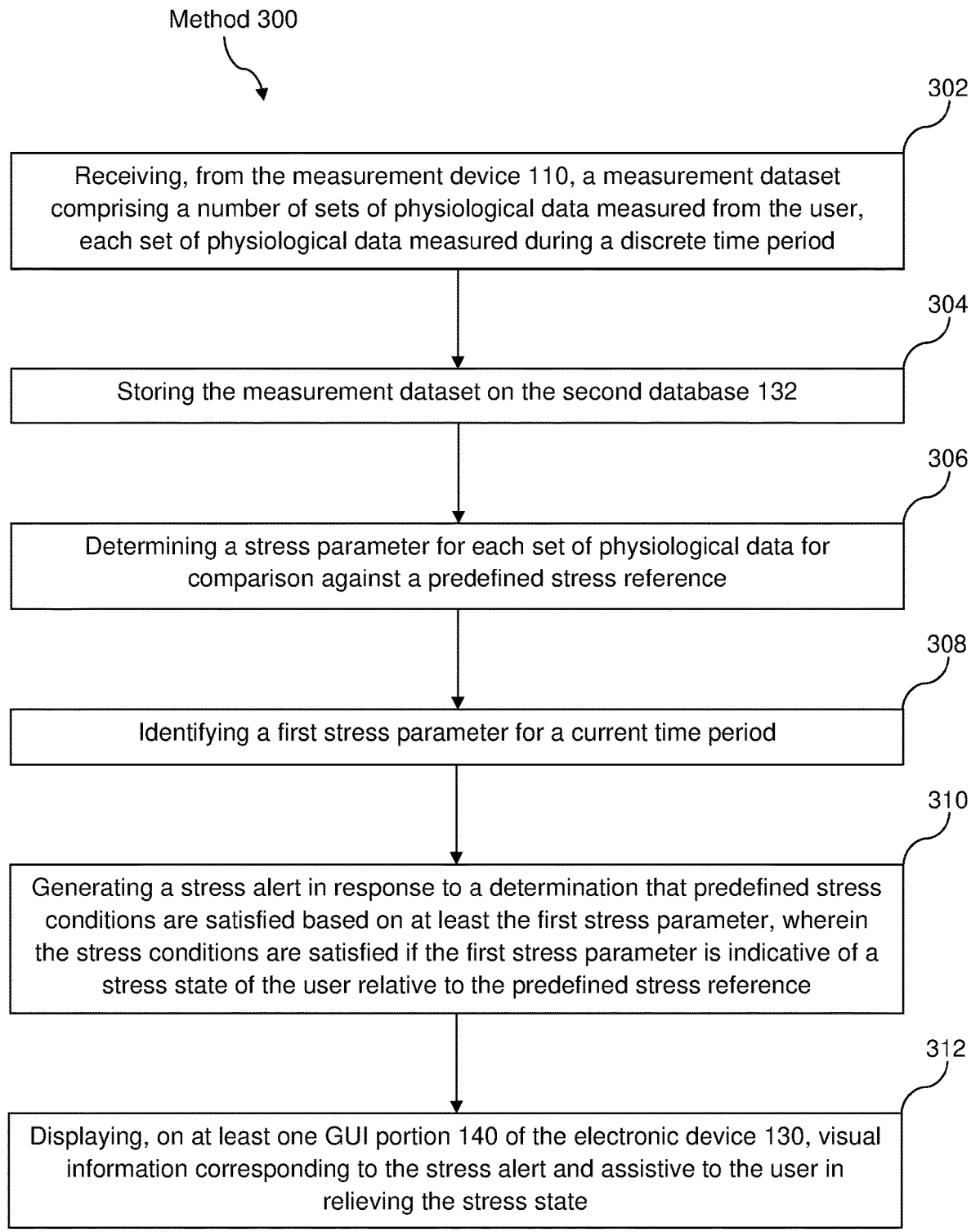
FIG. 3 is a flowchart illustration of a computerized method performed by the electronic device for stress assessment of the user, in accordance with embodiments of the present disclosure.

With reference to FIG. 3, there is shown a computer-implemented or computerized method 300 for stress assessment of the user. The method 300 is implemented on and performed by the electronic device 130 which comprises various modules/components, including a processor for executing program instructions, for performing various steps of the method 300.

The method 300 includes a step 302 of receiving, from the measurement device 110, a measurement dataset comprising a number of sets (i.e. at least one set) of physiological data measured from the user, each set of physiological data measured during a discrete time period. The method 300 includes a step 304 of storing the measurement dataset on the second database 132. The method 300 includes a step 306 of determining a stress parameter for each set of physiological data for comparison against a predefined stress reference. The method 300 includes a step 308 of identifying a first stress parameter for a current time period. The method 300 includes step 310 of generating a stress alert in response to a determination that predefined stress conditions are satisfied based on at least the first stress parameter. Specifically, the stress conditions are satisfied if the first stress parameter is indicative of a stress state of the user relative to the predefined stress reference. The method 300 includes a step 312 of displaying, on at least one GUI portion 140 of the electronic device 130, visual information corresponding to the stress alert and assistive to the user in relieving the stress state.

In the steps 202 and 302, the set(s) of physiological data are measured from the user using the measurement device 110 before the stress parameters are determined. Each set of physiological data is measured during a discrete time period which can range from 1 minute to 5 minutes, although other time periods are possible, such as 10 minutes, 30 minutes, 1 hour, etc. The duration of the discrete time periods may be adjustable by the user using the software application on the electronic device 130 or by using the measurement device 110. The set(s) of physiological data collectively form a series of physiological data. For example, the series of physiological data includes 12 sets of physiological data, wherein each set is measured during a discrete time period of 5 minutes, such that the series is measured during a time space of 1 hour. It will be appreciated that the discrete time period and number of sets in a series of physiological data are adjustable to customize the measurement of the physiological data to the user's preference.

In the steps 204 and 306, a stress parameter is determined for each set of physiological data in the respective time period for comparison against a predefined stress reference. The stress parameter may include a stress score or index that is calculated using a predefined algorithm applied to the physiological data such as heart rate, heart rate variability, blood pressure, pulse shape variability, and the like and any combination thereof. The predefined stress reference may be a reference stress score or index that is derived from the reference conditions of the user determined during the registration procedure. Additionally, the stress reference of the user may be further defined based on a national average stress pattern and/or stress parameters and stress references from a population of users.

The steps 206 and 308 identify the first stress parameter for the current time period. The first stress parameter may be indicative of a stress state of the user relative to the predefined stress reference. For example, the user may be in the stress state if the first stress parameter is at or higher than the stress reference. Conversely, the user may be in the normal/unstressed state if the first stress parameter is lower than the stress reference.

The predefined stress reference may be adjustable by the user to vary the sensitivity of the stress state indication. For example, the user may increase the stress reference so that there is lower probability of a stress parameter being indicative of a stress state. The software application may provide a number of levels of the predefined stress reference for the user to select.

In some embodiments of the method 200/300, the predefined stress conditions are satisfied based on the first stress parameter and a second stress parameter. In one embodiment, the method 200/300 optionally includes a step of identifying the second stress parameter for a second time period preceding the current time period. The current time period is thus consecutive to the second time period. The stress conditions are satisfied if, additionally, the second stress parameter is indicative of a stress state of the user relative to the predefined stress reference.

In another embodiment, the method 200/300 optionally includes a step of identifying a recent stress state of the user based on the stress parameters for earlier time periods before the current time period, the recent stress state indicative by the second stress parameter for an earliest of the earlier time periods. The earliest time period wherein the second stress parameter indicates the stress state may immediately precede the current time period or before that. The stress conditions are satisfied if, additionally, the second stress parameter is indicative of the recent stress state of the user, and none of the stress parameters for the other earlier time periods is indicative of a normal state of the user.

In some embodiments of the method 200/300, the predefined stress conditions are satisfied based on the first stress parameter, a second stress parameter, and a third stress parameter. In one embodiment, the method 200/300 optionally includes a step of identifying the second stress parameter for a second time period preceding the current time period, and identifying the third stress parameter for a third time period preceding the second time period. The current, second, and third time periods are thus consecutive time periods. The stress conditions are satisfied if, additionally, both the second and third stress parameters are indicative of a stress state of the user relative to the predefined stress reference.

In another embodiment, the method 200/300 optionally includes a step of identifying two recent stress states of the user based on the stress parameters for earlier time periods before the current time period, the recent stress states indicative by second and third stress parameters for second and third time periods, respectively, within the earlier time periods, the third time period being an earliest of the earlier time periods. The stress conditions are satisfied if, additionally, both the second and third stress parameters are indicative of the recent stress states of the user, and none of the stress parameters for the other earlier time periods is indicative of a normal state of the user.

In some embodiments of the method 200/300, the predefined stress conditions are satisfied based on the first stress parameter and a plurality of recent stress parameters. The method 200/300 optionally includes identifying a plurality of recent stress states of the user based on the stress parameters for earlier time periods before the current time period, the recent stress states indicative by the plurality of recent stress parameters for a plurality of recent time periods within the earlier time periods, the plurality of recent stress parameters including an earliest stress parameter for an earliest of the earlier time periods. The stress conditions are satisfied if, additionally, all of the plurality of recent stress parameters are indicative of the recent stress states of the user, and none of the stress parameters for the other earlier time periods is indicative of a normal state of the user.

Collating two or more stress parameters that indicate stress states for two or more discrete time periods, e.g. consecutive time periods, allows for a stress pattern to be established for improved accuracy in determining whether the user is in a stress state. However, this chain of stress parameters would be broken if one of the stress parameters is indicative of a normal state of the user, thus disregarding the earlier stress parameters. For example, the stress parameters for all time periods before the current time period are disregarded for the stress conditions if the first stress parameter is indicative of a normal state of the user.

The measurement device 110 may determine measurement conditions for each set of physiological data. The measurement conditions may affect the accuracy of the measured physiological data. If the measurement conditions are determined to be unsatisfactory, such as if they do not satisfy the reference conditions of the user determined during the registration procedure or some other set of common reference conditions applicable to all measurement devices 110, the set of physiological data measured under these unsatisfactory measurement conditions are discarded. In one embodiment, discarding the physiological data may mean permanently deleting the physiological data. In another embodiment, the physiological data may still be stored on the first database 112 for subsequent communication to the electronic device 130 and remote server 150 but would not be considered for stress assessment. As the physiological data for this time period is discarded, the stress parameter for this time period cannot be determined. This would be indicative of an invalid or null state since it cannot be determined whether the user is in a stress or normal state. Absence of physiological data for a time period would also result in a null state.

Figure 4A:
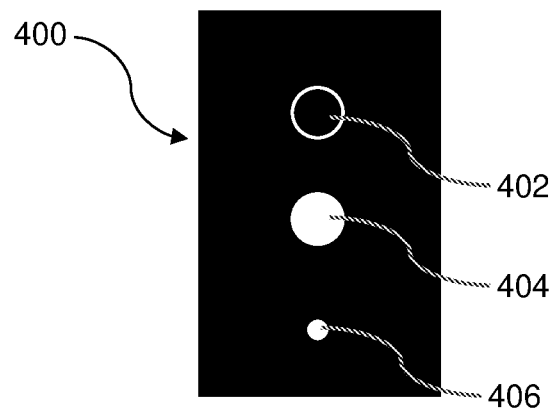
FIG. 4A to FIG. 4C are illustrations of graphics/screens displayed on the measurement device/electronic device for visual information, in accordance with embodiments of the present disclosure.
Figure 4B:
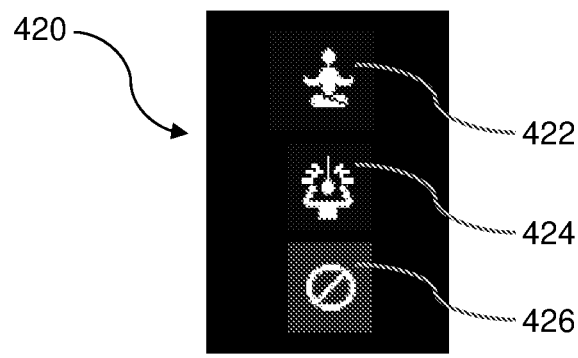
Figure 4C:
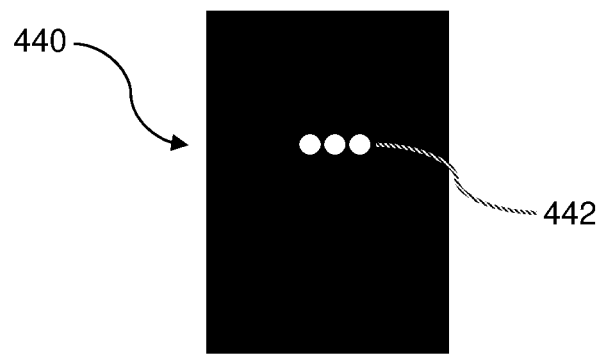

Each of the measurement device 110 and the electronic device 130 is configured to display various graphics/screens on the GUIs 118 and 138, respectively, during measurement of physiological data from the user and/or during processing of the physiological data for stress assessment. With reference to FIG. 4A to FIG. 4C, there is a first graphic 400, a second graphic 420, and a third graphic 440 displayable on the GUIs 118 and 138. The graphics 400/420/440 display visual information related to the stress assessment to the user. In the measurement device 110, the graphics 400/420/440 may be displayed on any of the GUI portions 120. Similarly, in the electronic device 130, the graphics 400/420/440 may be displayed on any of the GUI portions 140.

Visual information from the stress assessment may be presented to the user on the GUI 118/138. The visual information may include colour indicators of monochrome (black & white), grayscale, and/or colour palettes. During measurement of the physiological data in each time period, visual information may be presented to the user in the form of the first graphic 400 and/or second graphic 420. The first graphic 400 may be presented in monochrome or grayscale palette. The first graphic 400 as shown in FIG. 4A includes a normal icon 402 representing the normal/unstressed state, a stress icon 404 representing the stress state, and a null icon 406 representing the null state. The second graphic 420 may be presented in monochrome, grayscale, or colour palette. The second graphic 420 as shown in FIG. 4B includes a normal icon 422 representing the normal/unstressed state when the stress alert is not generated, a stress icon 424 representing the stress state when the stress alert is generated, and a null icon 426 representing the null state. The normal, stress, or null state for each time period is determined from processing of the physiological data as described above.

Figure 5A:
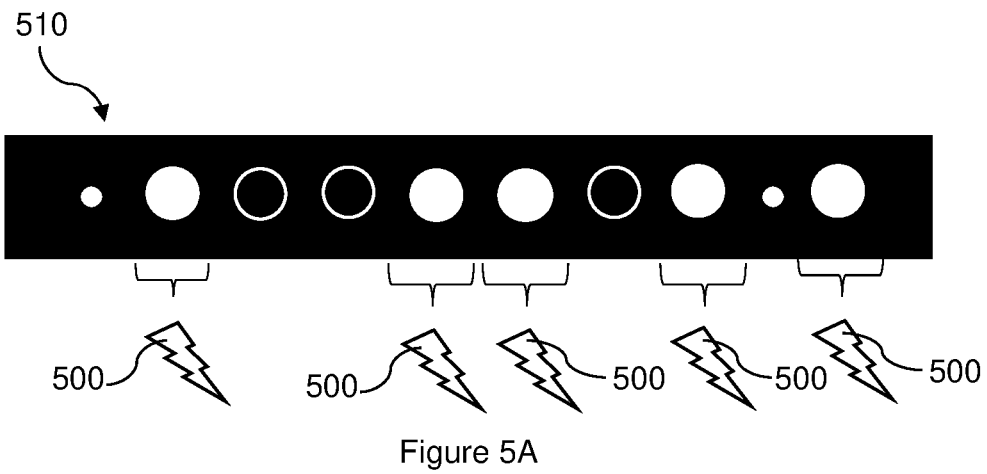
FIG. 5A to FIG. 5C are illustrations of time spaces having multiple consecutive discrete time periods for determining stress parameters to generate stress alerts, in accordance with embodiments of the present disclosure.

FIG. 5A illustrates an example of a time space 510 having multiple consecutive discrete time periods for which the stress parameters are determined. The series of stress parameters in the time space 510 may be displayed on the measurement device 110. Notably, the first to last time periods are arranged from right to left, and the first time period refers to the current time period. Each stress parameter is represented by the normal icon 402, stress icon 404, or null icon 406. A stress alert 500 is generated in response to a determination that predefined stress conditions are satisfied based on at least the first or current stress parameter. Specifically, the stress conditions are satisfied if the first stress parameter, which can be for any current time period, is indicative of the stress state. No stress alerts 500 are generated if the first stress parameter is indicative of the normal or null state.

Figure 5B:
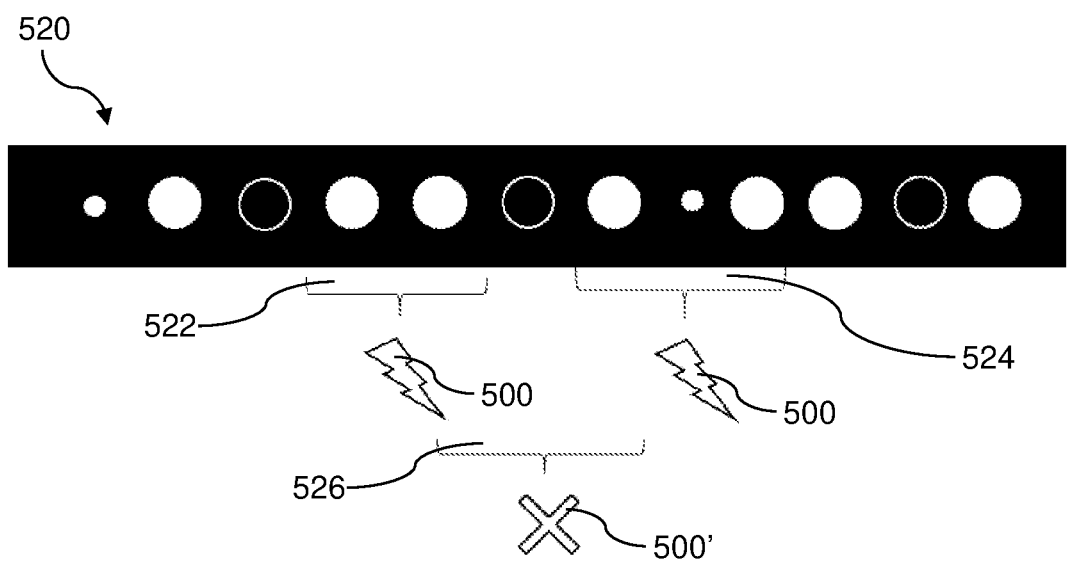

FIG. 5B illustrates another example of a time space 520 having multiple consecutive discrete time periods for which the stress parameters are determined. The series of stress parameters in the time space 520 may be displayed on the measurement device 110. In the time space 520, two stress parameters indicative of the stress state are generally required for the stress alert 500 to be generated, such as if there are stress states in two consecutive time periods. In a first group 522 of first and second time periods in the time space 520, both the first and second stress parameters are indicative of the stress state. The stress conditions are satisfied and the stress alert 500 is generated.

In a second group 524, the first stress parameter for the first time period is indicative of the stress state but the second stress parameter for the second time period is indicative of the null state. A recent stress state of the user is then identified based on the stress parameters for earlier time periods before the first time period. The recent stress state is indicative by a recent stress parameter for an earliest of the earlier time periods. In the second group 524, the recent stress parameter is the third stress parameter for the third time period, the third stress parameter indicative of the stress state. None of the stress parameters for the other earlier time periods (i.e. the second stress parameter for the second time period) is indicative of a normal state. The stress conditions are satisfied and the stress alert 500 is generated. Notably, the stress conditions would be satisfied and the stress alert 500 would be generated if the first and last stress parameters are indicative of the stress state, and the intervening stress parameters are not indicative of normal states, though they can be indicative of null states.

Indication of the normal state in any time period would "break" the chain of stress parameters for all earlier time periods leading to said time period and disregard the stress parameters for all earlier time periods. As an illustrative example, in a third group 526, the first and third stress parameters are indicative of the stress state, and the second stress parameter is indicative of the normal state. Although there are two stress parameters indicative of the stress state, the second stress parameter indicative of the normal state "breaks" the chain of stress parameters. Thus, the third stress parameter, as well as earlier stress parameters, is disregarded in determining if the stress conditions are satisfied. Since the stress state is indicative by the first stress parameter only, no stress alert 500 is generated, i.e. this would be a non-alert 500'. The stress alert 500 would be generated later in the next time period if the next stress parameter for the next time period is indicative of the stress state.

Figure 5C:
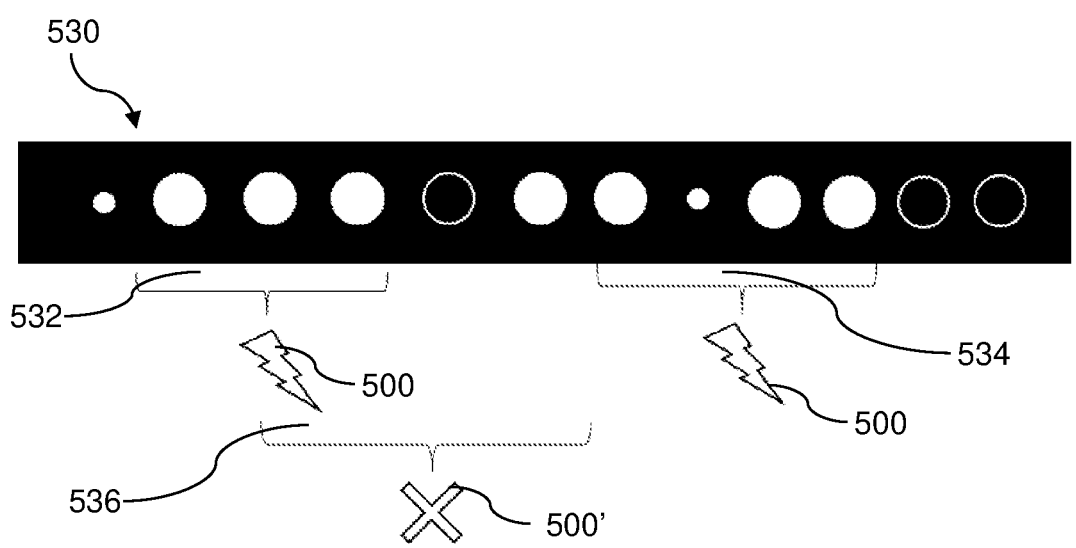

FIG. 5C illustrates another example of a time space 530 having multiple consecutive discrete time periods for which the stress parameters are determined. The series of stress parameters in the time space 530 may be displayed on the measurement device 110. In the time space 530, three stress parameters indicative of the stress state are generally required for the stress alert 500 to be generated, such as if there are stress states in three consecutive time periods. In a first group 532 of first to third time periods in the time space 530, all of the first to third stress parameters are indicative of the stress state. The stress conditions are satisfied and the stress alert 500 is generated.

In a second group 534, the first and second stress parameters for the first and second time periods are indicative of the stress state, but the third stress parameter for the third time period is indicative of the null state. Two recent stress states of the user are then identified based on the stress parameters for earlier time periods before the first time period. The recent stress states are indicative by two recent stress parameters for two recent time periods within the earlier time periods, one of the two recent time periods being an earliest of the earlier time periods. In the second group 534, the two recent stress parameters are the second and fourth stress parameters for the second and fourth time periods, both the second and fourth stress parameters indicative of the stress state. The fourth time period is also said one of the two recent time periods being the earliest of the earlier time periods. None of the stress parameters for the other earlier time periods (i.e. the third stress parameter for the third time period) is indicative of a normal state. The stress conditions are satisfied and the stress alert 500 is generated. Notably, the stress conditions would be satisfied and the stress alert 500 would be generated if the first and last stress parameters are indicative of the stress state, and the intervening stress parameters include one that is indicative of the stress state and none that is indicative of the normal state, though they can be indicative of the null state.

Similar to the time space 520 in FIG. 5B, indication of the normal state in any time period would break the chain of stress parameters for all earlier time periods leading to said time period and disregard the stress parameters for all earlier time periods. As an illustrative example, in a third group 536, the first, third, and fourth stress parameters are indicative of the stress state, and the second stress parameter is indicative of the normal state. Although there are three stress parameters indicative of the stress state, the second stress parameter indicative of the normal state breaks the chain of stress parameters. Thus, the third and fourth stress parameters, as well as earlier stress parameters, are disregarded in determining if the stress conditions are satisfied. Since the stress state is indicative by the first stress parameter only, no stress alert 500 is generated, i.e. this would be a non-alert 500'. The stress alert 500 would be generated later in the second next time period if the two next stress parameters for the two next time periods are indicative of the stress state.

It will be appreciated that the user may configure/adjust the predefined stress conditions such that the stress alerts 500 are generated based on different combinations/permutations of the various stress parameters for various time periods. To illustrate this is a generic example, there is a generic time space having multiple consecutive discrete time periods for which the stress parameters are determined. In this generic time space, a plurality of stress parameters indicative of the stress state are generally required for the stress alert 500 to be generated, such as if there are stress states in a plurality of consecutive time periods. If there is no continuity of the stress states and the first stress parameter is indicative of the stress state, a plurality of recent stress states of the user are then identified based on the stress parameters for earlier time periods before the first time period. The recent stress states are indicative by a plurality of recent stress parameters for a plurality of recent time periods within the earlier time periods. The plurality of recent stress parameters include an earliest stress parameter for an earliest of the earlier time periods. The stress conditions are satisfied if the first stress parameter and all of the plurality of recent stress parameters are indicative of the recent stress states of the user, and none of the stress parameters for the other earlier time periods is indicative of a normal state of the user, since the normal state breaks the chain of stress parameters.

Figure 6:
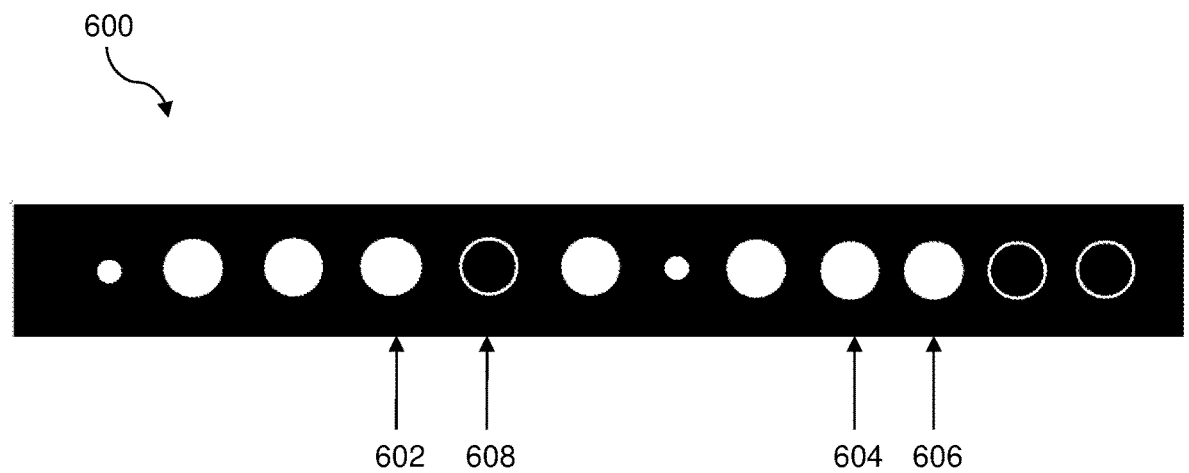
FIG. 6 is an illustration of a generic time space for determining stress parameters to generate stress alerts, in accordance with embodiments of the present disclosure.

Referring to the generic time space 600 in FIG. 6 as an illustrative example, if a total of three stress parameters (including the first stress parameter for the current time period) indicative of the stress state are required to satisfy the stress conditions and to generate the stress alert 500, the stress alert 500 would be generated in the current time periods 602, 604, and 606. If a total of four stress parameters indicative of the stress state are required, the stress alert 500 would be generated in the current time period 604 and 606. If a total of five stress parameters indicative of the stress state are required, the stress alert 500 would not be generated any time period in the time space 600. Notably, the stress parameter for the time period 608 (indicative of the normal state) would break the chain of stress parameters and disregard the stress parameter for the time period 602 (indicative of the stress state). However, if the stress parameter for the time period 608 is instead indicative of the stress or null state, then the stress alert 500 would be generated in the current time period 606.

Consideration of the stress parameters for multiple time periods in a time space helps to establish a stress or mood pattern of the user and more accurately informs the user of his/her overall stress state. It will be appreciated that additional stress parameters for additional preceding time periods can be considered collectively with the stress parameters for the later time periods to establish a longer-term or chronic stress pattern of the user.

In the steps 210 and 312, visual information corresponding to the stress alert 500 is displayed on at least one GUI portion 120/140. The visual information may be presented to the user in the form of the third graphic 440. The third graphic 440 may be presented in colour palette. The third graphic 440 includes a set of illumination elements (e.g. LEDs) 442. The third graphic 440 as shown in FIG. 4C includes three LEDs 442 arranged in a row, wherein the LEDs 442 are configured to illuminate the colour indicator. If there is no stress alert 500 generated, the colour indicator is green which indicates that the user is in a normal state or mood. Conversely, if a stress alert 500 is generated, the colour indicator of the visual information corresponding to the stress alert 500 is purple. Surprisingly, the purple colour indicator assists the user to calm down. Accordingly, if a stress alert 500 is generated because the user is in a stress state, the visual information corresponding to the stress alert 500 would be assistive to the user in relieving the stress state.

The third graphic 440 and/or another graphic containing visual information corresponding to the stress alert 500 may appear as a visual pop-up notification on the GUI 118/138 to attract the attention of the user. In some embodiments, the measurement device 110 comprises a haptic module for generating haptic feedback corresponding to the stress alert 500. The haptic feedback may be in the form of vibrations that can be felt by the user wearing the measurement device 110, thereby alerting the user to the stress state. The software application may avail functions for the user to configure the visual pop-up notification and haptic feedback, such as the visual appearance and vibration intensity.

The visual information is presented to the user in real-time based on live measurement of the physiological data. As the stress state may change constantly and is dependent on the user's physiological reaction, the visual information may appear quickly to assist the user in combating and managing stress. The visual information and optionally the haptic feedback resulting from the stress alert 500 help the user to be aware of their stress states and encourage the user to take action to reduce their stress state.

As described above, a time space, such as the time spaces 510/520/530 shown in FIG. 5A to FIG. 5C, has multiple consecutive discrete time periods. Each time period identically ranges from 1 minute to 5 minutes, although other ranges are possible. Various discrete time periods may have identical duration but may alternatively differ from one another. A series of physiological data is measured during the time space and the series of physiological data are collectively considered in determining the stress state of the user. Measurement of the series of physiological data by the measurement device 110 during a single time space may be known as spot stress measurement.

When the measurement device 110 performs a new spot stress measurement, the new physiological data is stored as a first series of physiological data on the first database 112. The first series of physiological data may be shared with the electronic device 130 and/or remote server 150 for further processing. For example, the first series of physiological data is communicated to the electronic device 130 for further processing, such as for archiving because the first database 112 is unable to store more than one series of physiological data. The first series of physiological data may then be stored on the second database 132. The second database 132 may already have preceding series of physiological data that were measured earlier, such as a second and third series of physiological data. The multiple series of physiological data may be collectively processed by the electronic device 130 to determine an intermediate stress measurement and a cumulative stress pattern.

Figure 7A:
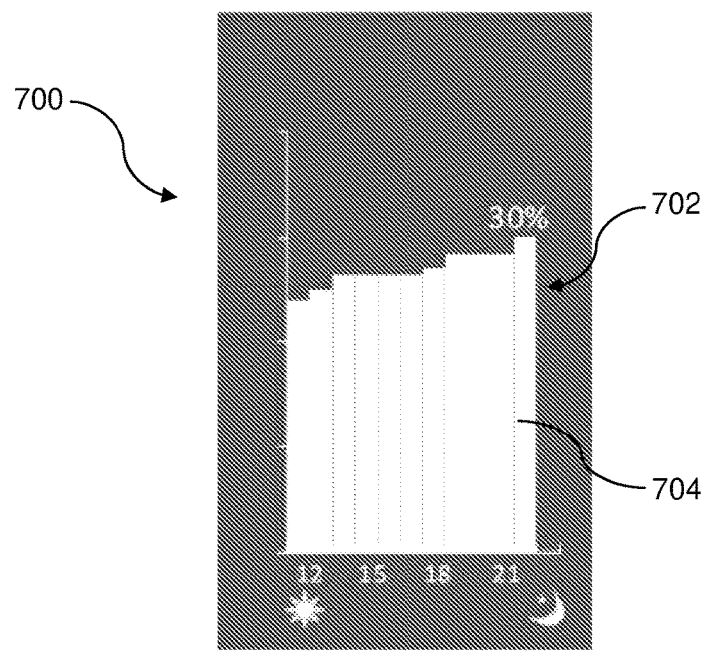
FIG. 7A and FIG. 7B are illustrations of a histogram graphic/screen displayed on the electronic device for visualization of a cumulative stress pattern of the user, in accordance with embodiments of the present disclosure.

In one embodiment as shown in FIG. 7A, the electronic device 130 may display a histogram graphic/screen 700 on the GUI 138 for visualization of the cumulative stress pattern 702 of the user. The cumulative stress pattern 702 is formed from several time spaces. Each time space is associated with a cumulative stress parameter determined from the series of physiological data measured during the time space. The cumulative stress parameter for the time space may be determined based on a mean or median of the stress parameters for the time periods within the time space. Accordingly, the cumulative stress pattern 702 as shown in the histogram graphic 700 is determined from the cumulative stress parameters and provides visual information or feedback to the user the intermediate stress measurement of the user. The histogram graphic 700 helps the user to be more aware of his/her mood and stress pattern.

Figure 7B:
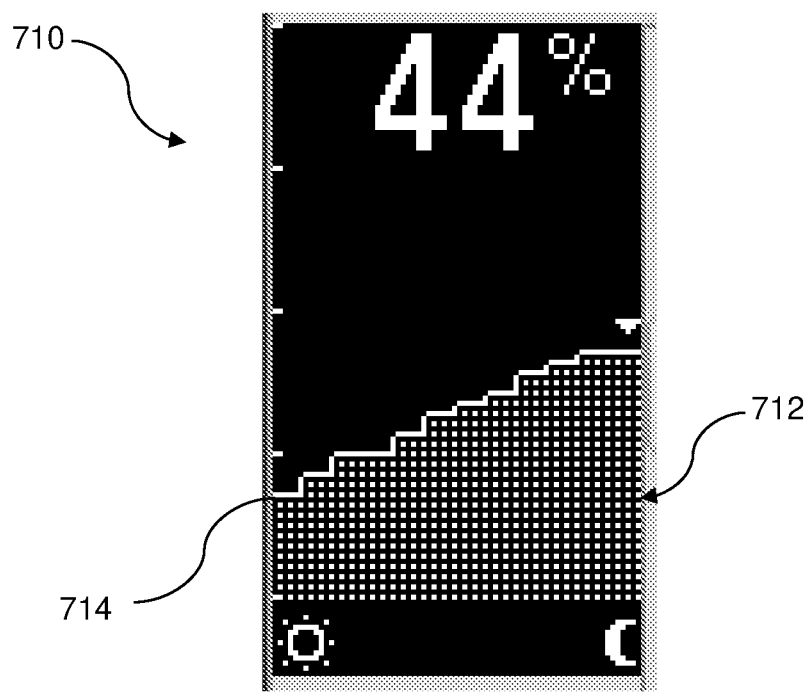

In FIG. 7A, the histogram graphic 700 shows the cumulative stress pattern 702 for 12 hours of time spaces. Each bar or interval 704 in the cumulative stress pattern 702 represents or spans the time space of 1 hour. In another embodiment as shown in FIG. 7B, the electronic device 130 may display an alternative histogram graphic/screen 710 on the GUI 138 for visualization of the cumulative stress pattern 712 of the user. Instead of bars 704 in the histogram graphic 700, the histogram graphic 710 shows a chart line 714 across columns that represent the 12 hours of time spaces.

It will be appreciated that the cumulative stress pattern 702/712 may be displayed for any duration between 1 hour and 24 hours or longer. The cumulative stress pattern 702/712 may be updated with the cumulative stress parameter for a new time space. The leftmost or rightmost time space then shifts out of sight (i.e. out of the GUI 138) and the new time space is added to update the cumulative stress pattern 702/712. For example, the cumulative stress pattern 702 is displayed for 12 hours of time spaces from 0600 to 1800 hours. When the series of physiological data for the next hour is received, the cumulative stress parameter is determined and updated to the cumulative stress pattern 702/712. Specifically, the cumulative stress pattern 702/712 will shift to then display 12 hours of time spaces from 0700 to 1900 hours. Accordingly, the cumulative stress pattern 702/712 and the histogram graphic 700/710 may be updated every hour (or at any other time interval).

The user may configure the cumulative stress pattern 702/712 to display less or more than 12 hours of time spaces. For example, the cumulative stress pattern 702/712 may be displayed for one week or 168 hours of time spaces. Each bar or interval 704 in the cumulative stress pattern 702 or each column in the chart line 714 may represent or span the time space of 1 hour. The user may adjust visualization of the cumulative stress pattern 702/712 on the histogram graphic 700/710, such as by adjusting each bar or interval 704 of the cumulative stress pattern 702 or each column of the chart line 714. For example, each bar or interval 704 or each column may span 12 to 14 hours instead of 1 hour. The user may also reset the intermediate stress measurement and cumulative stress pattern 702/712 at any given time/intervals, e.g. daily or weekly or on predefined number of days, or at predefined times, e.g. end of each day.

In some embodiments, the user may configure the measurement device 110 to reset daily or weekly etc. as the first database 112 may not be able to store more physiological data. The measured physiological data may be transferred to the electronic device 130 and/or remote server 150 for further processing and for storing/archiving on the second database 132 and/or third database 152, respectively. Particularly, the remote server 150 may store historical physiological data of the user on the third database 152 for performing long-term stress measurement, such as to determine a long-term or chronic stress pattern.

In one embodiment, the remote server 150 receives a measurement dataset from the measurement device 110 or the electronic device 130. The measurement dataset comprises a plurality of sets of physiological data measured from the user. The measurement dataset is stored on the third database 152 together with historical measurement datasets of the user obtained previously. The measurement datasets of the user may be collectively used to derive various information of the user. For example, the remote server 150 may apply algorithms to the measurement datasets to calculate a user activity, a user sleep activity, a user stress parameter, etc. The total duration of the long-term measurement, i.e. of all the time spaces from all the measurement datasets, may range from days to years as adjustable by the user. Various algorithms and statistical approaches may be implemented to perform the long-term stress measurement based on all the measurement datasets. The user may request for periodic overviews of the measurement datasets and long-term stress patterns, such as in daily, weekly, or monthly formats. The periodic overviews may be communicated to the measurement device 110/electronic device 130 and displayed on the GUIs 118/138, respectively.

In some embodiments, the remote server 150 determines a long-term or chronic stress state of the user from the long-term stress measurement and relative to a reference dataset. The reference dataset may be derived from derived from the reference conditions of the user, a national average, and/or a user population. The remote server 150 additionally generates recommendation content for relieving the chronic stress state of the user. Recommendation content may be provided by third party service providers and shared with the remote server 150. Based on the measurement datasets of a particular user, the remote server 150 and generate curated recommendation content and distribute it to the user. Some non-limiting examples of the recommendation content include relaxation methods (e.g. breathing exercises and mindfulness training), stress relief images/videos/audio, interactive information, exercise/fitness information (e.g. Yoga and Pilates), and suggested foods/supplements for stress relief. The recommendation content may be communicated to the measurement device 110/electronic device 130 and displayed on the GUIs 118/138, respectively.

In some embodiments, there are active communication links through the communication network 170 among the measurement device 110, electronic device 130, and remote server 150. The active communication links facilitate automatic sharing of the physiological data immediately or shortly after measurement by the measurement device 110. In this manner, stress assessment of the user based on the physiological data be performed by the measurement device 110, electronic device 130, and remote server 150 in real-time. The user can similarly obtain visual information from the stress assessment in real-time.

In one embodiment, clinicians can communicate with the remote server 150 to access the stress assessment of a particular user, such as one who has been previously assessed by clinicians to be at risk of being chronically stressed. The long-term stress measurement performed by the remote server 150 provides the clinicians with a more accurate and insightful long-term stress pattern of the user. The long-term stress pattern helps the clinicians to check on the user's state of mind and may give the clinicians a view of the user's stress pattern over time. The clinicians may administer appropriate stress relaxation exercises or in very severe conditions, administer medication to the user. Clinicians may also take the long-term stress pattern into consideration when assessing other health conditions of the user, such as hypertension and sleep-related conditions.

As described above, absence of physiological data for a time period would result in a null state. In one embodiment, the null state would cause a null signal to be communicated from the measurement device 110 to the electronic device 130/remote server 150. The null signal alerts the clinicians to the condition where no physiological data is available for the time period. The remote server 150 can track the measurement of physiological data in real-time and if there is no physiological data received for a particular time period, this might lead the clinicians to deduce adverse conditions for the user. For example, as some users may experience extreme stress states, the clinicians may deduce that the user is in distress, such as in a suicidal condition or a situation where the user may cause self-harm or hurt others. In a more specific example, the user may be wearing the measurement device 110 (in the form of a watch) on the wrist and the measurement device 110 is continuous measuring physiological data. However, the next time period results in the null signal which could mean that the user might have slit his/her wrist, causing profuse bleeding from the wrist and changes in the measurement of physiological data, such as sudden termination of the measurement. The null signal helps the clinicians to assess whether the user is in distress and determine whether immediate remedy action is necessary.

Figure 8:
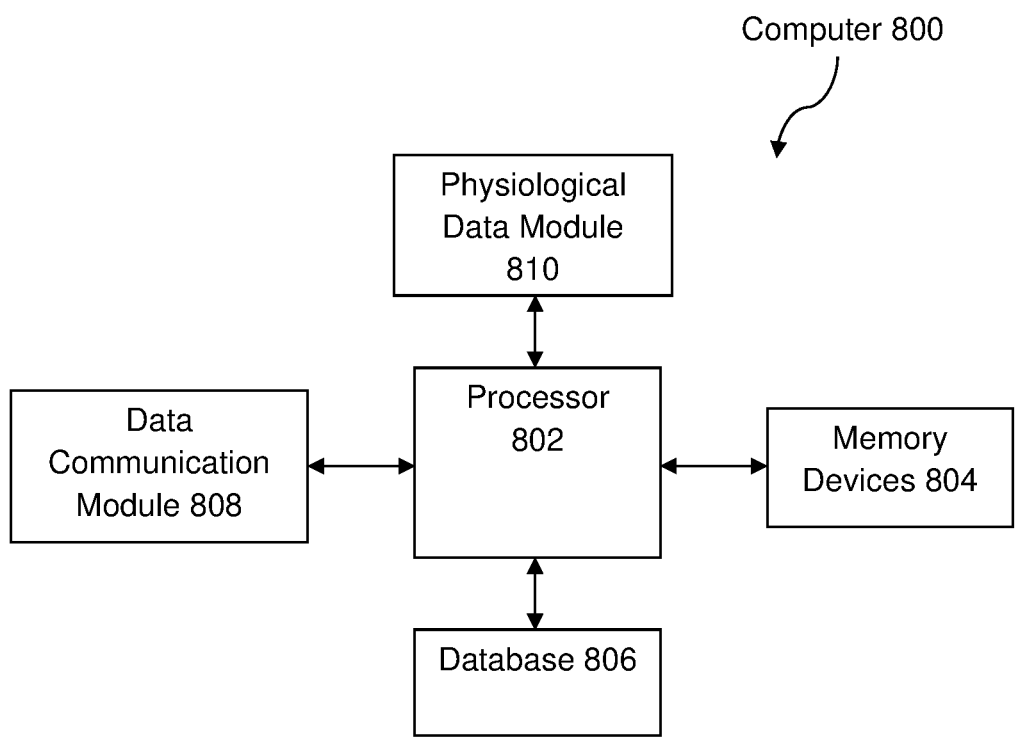
FIG. 8 is a block diagram illustration of the technical architecture of a computer, in accordance with embodiments of the present disclosure.

FIG. 8 is a block diagram illustrating a technical architecture of a computer 800 in accordance with embodiments of the present disclosure. Some non-limiting examples of the computer 800 are the measurement device 110, electronic device 130, and remote server 150. The computer 800 includes a processor/central processing unit (CPU) 802, memory devices 804, a database 806, a data communication module 808, and a physiological data module 810.

The processor 802 executes instructions, codes, computer programs, and/or scripts which it accesses from the memory devices 804. The processor 802 includes suitable logic, circuitry, and/or interfaces to execute such operations or steps. Some non-limiting examples of the processor 802 include an application-specific integrated circuit (ASIC) processor, a reduced instruction set computing (RISC) processor, a complex instruction set computing (CISC) processor, a field-programmable gate array (FPGA), and the like. While only one processor 802 is shown, multiple processors 802 may be present. Thus, while instructions may be discussed as executed by a processor 802, the instructions may be executed simultaneously, serially, or otherwise executed by one or multiple processors 802 (e.g. in a multi-core configuration).

The memory devices 804 may comprise storage devices (such as flash memory, disk drives, or memory cards), read-only memory (ROM), and random-access memory (RAM). The memory devices 804 store non-transitory instructions operative by the processor 802 to perform various operations or steps of the methods 200/300 according to various embodiments of the present disclosure. The memory devices 804 may be referred to as computer-readable storage media and/or non-transitory computer-readable media. Non-transitory computer-readable media include all computer-readable media, with the sole exception being a transitory propagating signal per se.

The database 806 is any computer-operated hardware suitable for storing and/or retrieving data. Some non-limiting examples of the database 806 are the databases 112, 132, and 152. The database 806 may include multiple storage units such as hard disks and/or solid-state disks in a Redundant Array of Independent Disks (RAID) configuration. The database 806 may include, but is not limited to, a storage area network (SAN) and/or a network attached storage (NAS) system. The data communication module 808 is configured for communication with other computers 800.

The physiological data module 810 is configured to process the physiological data and to perform stress assessment based on the physiological data. Various algorithms may be implemented in the physiological data module 810 for performing said processing of the physiological data and said stress assessment.

In the foregoing detailed description, embodiments of the present disclosure in relation to devices and methods for stress assessment are described with reference to the provided figures. The description of the various embodiments herein is not intended to call out or be limited only to specific or particular representations of the present disclosure, but merely to illustrate non-limiting examples of the present disclosure. The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the disclosure as well as the scope of the following claims is not limited to embodiments described herein.

The invention claimed is:

1. A wearable measurement device for stress assessment of a user, comprising:
a sensor module comprising a photoplethysmography (PPG) sensor for measuring, from the user, a number of sets of physiological data, each set of physiological data measured during a discrete time period;
a database for storing the physiological data;
a display module comprising a set of graphical user interface (GUI) portions for displaying visual information from the stress assessment based on the physiological data; and
a processor configured for:
determining a stress parameter from each set of physiological data for comparison against a predefined stress reference;
identifying a plurality of stress parameters in a time space having a plurality of consecutive discrete time periods, each stress parameter for one of the time periods, the plurality of stress parameters including a first stress parameter for a current time period ending the time space and one or more earlier stress parameters for one or more earlier time periods before the current time period;
generating a stress alert in response to a determination that predefined stress conditions are satisfied based on a consecutive plurality of stress parameters including the first stress parameter and a second stress parameter for a time period immediately preceding the current time period, wherein the stress conditions are satisfied if each of the first stress parameter and the second stress parameter is indicative of a stress state of the user relative to the predefined stress reference; and communicating the stress alert to the display module for displaying, on at least one of the GUI portions, the visual information corresponding to the stress alert and assistive to the user in relieving the stress state, wherein the stress conditions are associated with a stress pattern of the user formed by the plurality of stress parameters in the time space.

2. The device according to claim 1, wherein the plurality of stress parameters includes an earliest stress parameter for an earliest time period starting the time space; and wherein the stress conditions are satisfied if each of the first and earliest stress parameters is indicative of the stress state of the user, and none of the other earlier stress parameters is indicative of a normal state of the user.

3. The device according to claim 1, wherein the plurality of stress parameters further includes a third stress parameter for a third time period preceding the second time period; and wherein the stress conditions are satisfied if each of the first, second, and third stress parameters is indicative of the stress state of the user relative to the predefined stress reference.

4. The device according to claim 1, wherein stress parameters for all time periods before the current time period are disregarded for the stress conditions if the first stress parameter is indicative of a normal state of the user.

5. The device according to claim 1, wherein the processor is further configured for communicating the sets of physiological data to an electronic device and/or a remote server for processing by the electronic device and/or the remote server, respectively.

6. The device according to claim 1, further comprising a haptic module for generating haptic feedback corresponding to the stress alert.

7. The device according to claim 1, wherein the processor is further configured for determining measurement conditions for each set of physiological data.

8. The device according to claim 1, wherein the predefined stress reference and/or predefined stress conditions is adjustable by the user.

9. A computerized method for stress assessment of a user, the method performed by a wearable measurement device and comprising:

retrieving, from a database of the wearable measurement device, a number of sets of physiological data measured from the user, each set of physiological data measured during a discrete time period;

determining a stress parameter from each set of physiological data for comparison against a predefined stress reference;

identifying a plurality of stress parameters in a time space having a plurality of consecutive discrete time periods, each stress parameter for one of the time periods, the plurality of stress parameters including a first stress parameter for a current time period ending the time space and one or more earlier stress parameters for one or more earlier time periods before the current time period;

generating a stress alert in response to a determination that predefined stress conditions are satisfied based on a consecutive plurality of stress parameters including the first stress parameter and a second stress parameter for a time period immediately preceding the current time period, wherein the stress conditions are satisfied if each of the first stress parameter and the second stress parameter is indicative of a stress state of the user relative to the predefined stress reference; and displaying, on at least one graphical user interface (GUI) portion, visual information corresponding to the stress alert and assistive to the user in relieving the stress state, wherein the stress conditions are associated with a stress pattern of the user formed by the plurality of stress parameters in the time space.

10. The method according to claim 9, wherein the plurality of stress parameters includes an earliest stress parameter for an earliest time period starting the time space; and wherein the stress conditions are satisfied if each of the first and earliest stress parameters is indicative of the stress state of the user, and none of the other earlier stress parameters is indicative of a normal state of the user.

11. The method according to claim 9, wherein the plurality of stress parameters further includes a third stress parameter for a third time period preceding the second time period; and wherein the stress conditions are satisfied if each of the first, second, and third stress parameters is indicative of the stress state of the user relative to the predefined stress reference.

12. The method according to claim 9, wherein stress parameters for all time periods before the current time period are disregarded for the stress conditions if the first stress parameter is indicative of a normal state of the user.

13. The method according to claim 9, further comprising communicating the sets of physiological data to an electronic device and/or a remote server for processing by the electronic device and/or the remote server, respectively.

14. A computerized method for stress assessment of a user, the method performed by an electronic device and comprising:

receiving, from a wearable measurement device, a measurement dataset comprising a number of sets of physiological data measured from the user, each set of physiological data measured during a discrete time period;

storing the measurement dataset on a database of the electronic device;

determining a stress parameter from each set of physiological data for comparison against a predefined stress reference;

identifying a plurality of stress parameters in a time space having a plurality of consecutive discrete time periods, each stress parameter for one of the time periods, the plurality of stress parameters including a first stress parameter for a current time period ending the time space and one or more earlier stress parameters for one or more earlier time periods before the current time period;

generating a stress alert in response to a determination that predefined stress conditions are satisfied based on a consecutive plurality of stress parameters including the first stress parameter and a second stress parameter for a time period immediately preceding the current time period, wherein the stress conditions are satisfied if each of the first stress parameter and the second stress parameter is indicative of a stress state of the user relative to the predefined stress reference; and displaying, on at least one graphical user interface (GUI) portion, visual information corresponding to the stress alert and assistive to the user in relieving the stress state, wherein the stress conditions are associated with a stress pattern of the user formed by the plurality of stress parameters in the time space.

15. The method according to claim 14, wherein the plurality of stress parameters includes an earliest stress parameter for an earliest time period starting the time space, wherein the stress conditions are satisfied if each of the first and earliest stress parameters is indicative of the stress state of the user, and none of the other earlier stress parameters is indicative of a normal state of the user.

16. The method according to claim 14, wherein the plurality of stress parameters further includes a third stress parameter for a third time period preceding the second time period; and wherein the stress conditions are satisfied if each of the first, second, and third stress parameters is indicative of the stress state of the user relative to the predefined stress reference.

17. The method according to claim 14, wherein stress parameters for all time periods before the current time period are disregarded for the stress conditions if the first stress parameter is indicative of a normal state of the user.

18. The method according to claim 14, further comprising communicating the stress alert to the wearable measurement device for displaying corresponding visual information on the wearable measurement device.

19. The method according to claim 14, further comprising communicating the measurement dataset to a remote server for processing by the remote server.

20. The method according to claim 19, further comprising receiving, from the remote server, recommendation content for relieving a chronic stress state of the user, wherein the recommendation content is generated by and the chronic stress state is determined by the remote server based on the measurement dataset and historical measurement datasets of the user relative to a reference dataset.

\* \* \* \* \*